(12) United States Patent
Knudsen (10) Patent No.: US 10,137,261 B2
(45) Date of Patent: Nov. 27, 2018

(54) INHALATOR

(75) Inventor: Carsten Leonhard Knudsen, Neksø (DK)

(73) Assignee: LK INVESTMENT APS, Humlebaek (DK)

( * ) Notice: Subject to any disclaimer, the term of this patent is extended or adjusted under 35 U.S.C. 154(b) by 780 days.

(21) Appl. No.: 13/582,032

(22) PCT Filed: Mar. 4, 2011

(86) PCT No.: PCT/DK2011/050067
§ 371 (c)(1),
(2), (4) Date: Nov. 9, 2012

(87) PCT Pub. No.: WO2011/107104
PCT Pub. Date: Sep. 9, 2011

(65) Prior Publication Data
US 2013/0056005 A1   Mar. 7, 2013

(30) Foreign Application Priority Data

Mar. 4, 2010   (DK) .............................. 2010 70084
May 31, 2010   (DK) .............................. 2010 70227

(51) Int. Cl.
*A61M 15/06*   (2006.01)
*A61M 15/00*   (2006.01)
(Continued)

(52) U.S. Cl.
CPC ............. *A61M 15/06* (2013.01); *A61M 15/08* (2013.01); *Y10T 29/49872* (2015.01)

(58) Field of Classification Search
None
See application file for complete search history.

(56) References Cited

U.S. PATENT DOCUMENTS 5,144,962 A * 9/1992 Counts ................. A24F 47/008
                                                128/200.14
5,287,850 A * 2/1994 Haber et al. ............. 128/203.21
(Continued)

FOREIGN PATENT DOCUMENTS

DE     4338884 C1    3/1995
DK     174521 B1     5/2003
(Continued)

OTHER PUBLICATIONS

International Search Report received for PCT Patent Application No. PCT/DK2011/050067, dated Mar. 23, 2011, 4 pages.
(Continued)

*Primary Examiner* — (Jackie) Tan-Uyen T Ho
*Assistant Examiner* — Joseph D Boecker
(74) *Attorney, Agent, or Firm* — Morrison & Foerster LLP (57) ABSTRACT

An inhalator includes a housing with first and second compartments, and a substance. The second second compartment has an air entry port, the inhalator has a first end proximal to the first compartment and second end proximal to the second compartment, and the inhalation part is at the second end. The first compartment stores a substance and has in an inoperative state of the inhalator sealing bodies to define a sealed chamber for containing a substance. The bodies are movable together with the substance from the first compartment into the second compartment to define an inoperative state of the inhalator. Air enters through the air entry port and takes up, such as by evaporation, the substance contained in the second compartment. A release device moves the bodies into the second compartment and allows the air to flow to the air entry port in the operative state.

31 Claims, 4 Drawing Sheets

(51) Int. Cl.
*A61M 16/00* (2006.01)
*A61M 15/08* (2006.01)

(56) References Cited

U.S. PATENT DOCUMENTS

| | | | | |
|---|---|---|---|---|
| 5,881,721 | A | * | 3/1999 | Bunce et al. ............. 128/203.21 |
| 6,681,762 | B1 | * | 1/2004 | Scheuch et al. ......... 128/200.14 |
| 7,021,561 | B2 | * | 4/2006 | Vedrine et al. ................ 239/329 |
| 7,415,982 | B1 | | 8/2008 | Sheridan |
| 2003/0111552 | A1 | | 6/2003 | Vedrine et al. |
| 2005/0016550 | A1 | | 1/2005 | Katase |
| 2009/0062745 | A1 | * | 3/2009 | Qiu ....................... A61M 5/322 604/197 |
| 2009/0223515 | A1 | * | 9/2009 | Watanabe ............. A61M 11/00 128/203.15 |
| 2009/0297253 | A1 | * | 12/2009 | Yuu ................... A46B 11/0055 401/277 |

FOREIGN PATENT DOCUMENTS

| | | | |
|---|---|---|---|
| EP | 1867357 A1 | 12/2007 | |
| EP | 2 002 856 | * 12/2008 | ............ A61M 16/06 |
| EP | 2002856 A1 | 12/2008 | |
| WO | 2007/090594 A1 | 8/2007 | |

OTHER PUBLICATIONS

Search Report issued for Danish Patent Application No. 201000084, dated Aug. 19, 2010.
Search Report issued for Danish Patent Application No. 201070227, dated Aug. 19, 2010.
Search Report issued for Danish Patent Application No. 201070228, dated Aug. 19, 2010.
International Preliminary Report on Patentability received for PCT Patent Application No. PCT/DK2011/050067, dated Sep. 13, 2012, 8 pages.
Written Opinion received for PCT Patent Application No. PCT/DK2011/050067, dated Mar. 23, 2011, 6 pages.
Extended European Search Report received for European Patent Application No. 11750219.5, dated Jun. 19, 2015, 6 pages.
Office Action received for European Patent Application No. 11750219.5, dated Dec. 12, 2017, 9 pages.

* cited by examiner

FIG. 2a
DETAIL A

FIG. 3a
DETAIL B

DETAIL: Y-Y

INHALATOR

CROSS REFERENCE TO RELATED APPLICATIONS

This is a U.S. National Phase patent application of PCT/DK2011/050067, filed Mar. 4, 2011, which claims priority to the Danish Patent Applications No. PA 2010 70084, filed Mar. 4, 2010, and No. PA 2010 70227, filed May 31, 2010, each of which is hereby incorporated by reference in the present disclosure in its entirety.

The present invention relates to an improved inhalator. The inhalator may allow two or more substances to be packed such that they do not interact until the inhalator is brought to an operative state.

Often there is a need to store two or more reactive substances together but separated, e.g. two component glue, penicillin and water or interactive substances. When mixed, such substances will often initiate a reaction.

It is known that reactive substances when mixed can degrade each other by oxidation, reduction or by forming combination products. Likewise, the presence of air can sometimes interact with substances in an unwanted way. In connection with inhalers where two or more substances need to be mixed and inhaled it is often necessary to store the substances separately prior to inhalation.

EP 2002856 discloses an inhalator comprising a number of elastic bodies or spheres elastically restrained in a duct. Prior to use, the substance or substances, which are to be released and inhaled by the user, are kept in the chambers defined by the space between two or more spheres. The inhaler can be activated by inserting a pin into the duct container, and the pin will push the elastic spheres into the end piece. Substances previously kept in different chambers are thus allowed to mix and blend and are exposed to air whereby the different drugs or substances evaporate and are made available for the user to inhale. The pin is then removed whereby a free passage of air is provided, and the user can inhale the substances through the mouth piece. The spheres are made of for instance compressible silicone, rubber, neoprene or the like. In some applications, the use of a special skin forming, cell foamed silicone can be advantageous.

The above inhalator has been shown to give rise to i.a. the following problems.
  the pin must be discarded;
  a high air flow through the inhalator leads to an inefficient use of the stored substances;
  liquid present in the inhalator may flow out of the inhalator through the end opposite the mouth piece;
  inefficient and incomplete spending of some of the substances.

It is an object of the present invention to provide an improved inhalator i.e. solving the above problems.

This is achieved by an inhalator for storing a substance, preferably several substances to be mixed with each other, and comprising a housing with at least a first compartment and a second compartment, and including one or more substances, said second compartment including at least one air entry port, said inhalator having a first end proximal to said first compartment and a second end proximal to said second compartment, an inhalation part being at said second end, said first compartment being for storing at least one substance and including in an inoperative state of said inhalator a plurality of sealing bodies arranged in a neighboring relationship, each pair of neighboring bodies defining at least in part a sealed chamber for containing a substance, said bodies being movable together with said at least one substance from said first compartment into said second compartment to define an operative state of said inhalator wherein said one or more substances are contained in said second compartment, whereby air entering through said air entry port and taking up, such as by evaporation, said at least one substance when contained in said second compartment may be inhaled through said inhalation part, and by having a release device in said first compartment, said release device being for moving said bodies into said second compartment and allowing said air to flow to said air entry port in said operative state.

In one embodiment the inhalator includes a pin-shaped release device arranged or arrangeable in the first compartment and being for moving the bodies into the second compartment and allowing air to flow to said air entry port in said operative state. The release device defines a valve allowing the user to regulate the flow of said air entering the second compartment through the air entry port, and may even allow the user to choose between at least two values greater than zero of said flow of air entering through. The release device has a groove with a varying or increasing cross sectional area, thereby the air flow can be regulated by varying the extent of which the release device is pushed into the first compartment. The release device has a concave end opposite the head.

In another embodiment the second compartment having a cylindrical wall defining a surface configured to control the movement within said second compartment of said bodies; this may be by the surface including inwardly extending projections defining pointed tips for facing the bodies in the operative state of the inhalator.

The projections will form points or edges to which the bodies covered by the substance(s) will adhere by surface tension. Thus, an enhanced mixing of the substances with the air is obtained in that a larger surface of the bodies is exposed to the air in comparison to the solution disclosed in EP 2002856. These aspects may be benefited from independently of the features defined in the characterizing portion of claim 1.

In a third embodiment one of the substances being tobacco, said tobacco being in the form of at least one tobacco leaf.

The tobacco may be contained in said second compartment already in the inoperative state of the inhalator, or in one of said chambers, preferably one closest to the second compartment, whereby the tobacco preferably in the operative state of the inhalator will become located next to the inhalation part.

One advantage of the invention is that the tobacco may dampen the movement of the sealing bodies as they move in the second compartment. In addition, substances released from the sealed chamber(s) and entering the second compartment may be deposited on the tobacco, especially when the latter is in the form of tobacco leaves, the tobacco providing an enlarged surface from which the substances may evaporate on air entering the second compartment. In addition, the tobacco may add further flavor to the air inhaled by the user. These aspects may be benefited from independently of the features defined in the characterizing portion of claim 1.

In another embodiment one of the chambers may include a tobacco leaf and another chamber nicotine. Dry substance such as dried spices and liquorice root and carnation/clove useful for partial absorption of any liquid substances may also be used.

According to other aspects of the inhalator defined in the preamble of claim 1, the inhalation part may be formed integral with the second compartment, and may include a wrapping, such as paper or foil, extending at least partially, preferably fully, around one or more, preferably all, of the inhalator part, the first compartment and/or the second compartment. When one or more of the inhalation part, the first compartment and the second compartment are not formed integral with one another the wrapping may be adapted to maintain the inhalator part, the first compartment and the second compartment in a contiguous relationship in extension of each other; the wrapping may be adhered to the surface of the inhalator. These aspects may be benefited from independently of the features defined in the characterizing portion of claim 1. The wrapping may carry indicia, such as a text message, and may in principle resemble the paper wrapping used for making conventional cigarettes.

The present invention further relates to a method for manufacturing the inhalator described above, comprising the steps of:
- providing a plurality of said bodies, said bodies being elastic,
- providing a framework having a fixture for an inhalator housing
- fixing said inhaler housing in said fixture;
- positioning a first elastic body in said first compartment by pushing said body into said compartment;
- dosing a first substance into said first compartment next to said first body;
- positioning a second elastic body in said first compartment next to said first substance while compressing said second body such that said substance is enclosed on said compartment formed by said first and second bodies.

Hereby a fast, cheap, and simple method for manufacturing an inhalator according to the present invention is provided.

The elastic bodies are preferably formed as spheres. Hereby slightly oversized silicone spheres or balls e.g. formed of rubber, plastic or silicone could be used as elastic bodies thereby creating a diffusion tight seal between the compartments—and thereby preventing fluid substance from diffusing out of the compartment and preventing air from entering the compartment.

The surface of the elastic bodies is preferably surface treated enhancing liquid adherence properties of the surface, such that liquid substance(s) will adhere to the surface. Hereby is achieved that liquid substances can easily evaporate when released from the first compartment as such liquid substances would adhere to the surface of the elastic bodies e.g. when pushed/pulled into a mixing compartment and due to a larger surface area of the elastic bodies. The surface of the elastic bodies might be surface treated in order to enhance liquid adherence properties of the surface in a number of different ways. The elastic bodies could for instance be produced of silicone or rubber having ancillary substances which would help liquid substances adhere to the surface. The elastic bodies could also be mechanically formed such that liquids would adhere to the surface—for instance such that the surface is granulated and/or rough. The surface treatment could also be a chemical treatment where a chemical substance has been provided onto the surface of the elastic bodies, and the chemical substance could then react with liquid substances and thereby improve the adherence properties.

If the inhaler is to be used as a smoke-free cigarette, i.e. for inhaling nicotine, it is advantageous to keep the nicotine substance without exposure to the air, whereby the durability of the product will be significantly longer. Further, if any aromatic substance or substances or helping agents are to be inhaled in combination with the nicotine, these aromatic substances are advantageously kept in one or more chambers separate from the nicotine substance. Such aromatic substances could be of the group of Beta damascenone, 4-oxo-beta-ionone, oxo-edulan I-II, 3-oxo-alpha-ionone, Dihydro-actionodiolide, Megastigmatrienones (4 isomer), different Carotinoide derivate and the helping agents could for instance be different air humidifying agents, pH regulating fluids (such as picrine acid or ammonia), propylene glycol, catalysts, emulsifiers, Tannin (astringent) or different naturopathic drugs.

The different parts and modules of the inhaler can be made of different plastic materials, Barex metal alloys, or silicone to give the user a more realistic feeling of holding and 'smoking' a cigarette, the inhaler is in one embodiment wrapped with cigarette and filter paper.

Other alternative embodiment of the invention is disclosed in the depend claims.

An embodiment of the invention will be described in the following with reference to the drawings wherein.

Figure 1A:
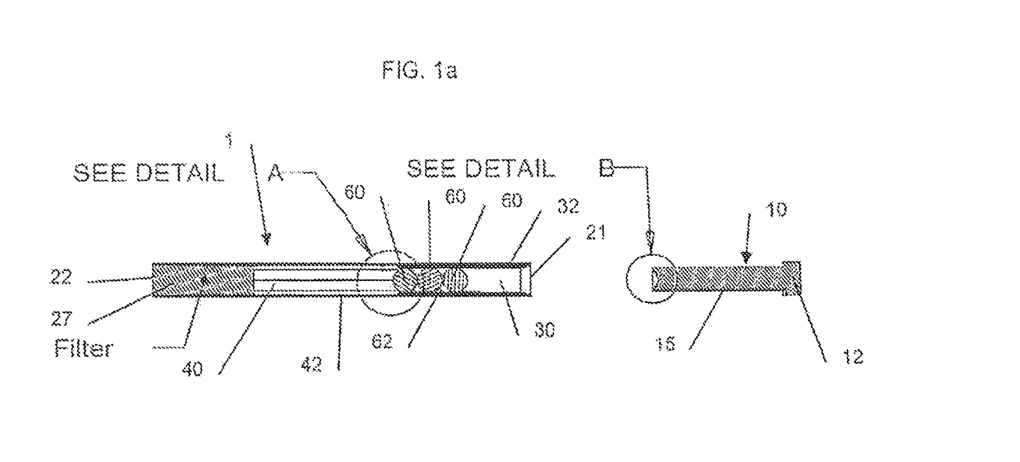
FIG. 1a is a schematic longitudinal cross-sectional view of the inhalator in the inoperative state, with the release device pulled out.
Figures 2A, 3A:
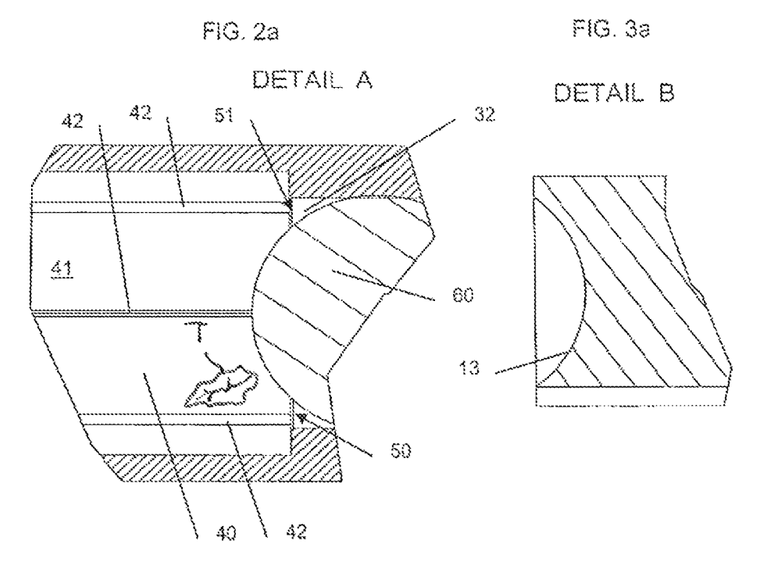
FIG. 2a is an enlarged longitudinal partial cross-section at the transition between the first and second compartments.
FIG. 3a is an enlarged longitudinal partial cross-section through the pin at one end opposite the head of the pin.

FIG. 1a shows in an inoperative state an inhalator (1) comprising an elongated cylindrical housing with a first compartment (30) and a second compartment (40); a typical size of the inhalator would be similar to that of a cigarette. The second compartment (40) includes at least one air entry port (50) at the transition between the first compartment and the second compartment (40), as shown in FIG. 2a, whereby any air flowing through the first compartment (30) may enter the second compartment (40). The inhalator (1) is preferably molded from a plastic material. As shown in FIG. 1a, a tobacco leaf T may be contained in the second compartment (40).

Preferably a single air entry port as shown is provided. However, an additional or alternative air entry port may be provided of the cylindrical wall (41) defining the second chamber 40 in which case this air entry port may be sealed prior to use of the inhalator.

The inhalator (1) has a first open end (21) proximal to the first compartment (30) and a second end (22) proximal to the second compartment (40), and an inhalation part (27) including a mouth-piece (not shown) for use by a person is located at the second end (22) whereby the user may inhale air in the second compartment (40). In the inoperative state the first compartment (30) stores two substances, such as a tobacco leaf and nicotine, a respective substance being in a respective sealed chamber (62) defined by the housing wall inside surface (32) and neighboring bodies (60). The chambers (62) are to the extent possible sealed from the outside environment; preferably, the bodies are elastic and held slightly compressed in the first compartment (30) to provide an effective seal with the inner surface of the wall (32) defining the first compartment (30). Preferably, if tobacco is stored in one of the chamber (62) this would be in a chamber closest to the second compartment (40) such that the tobacco is released into the second compartment (40) first. In this case no tobacco T may already be stored in the second compartment (40).

In another aspect tobacco can be stored within the same chamber as the nicotine.

Figure 1B:
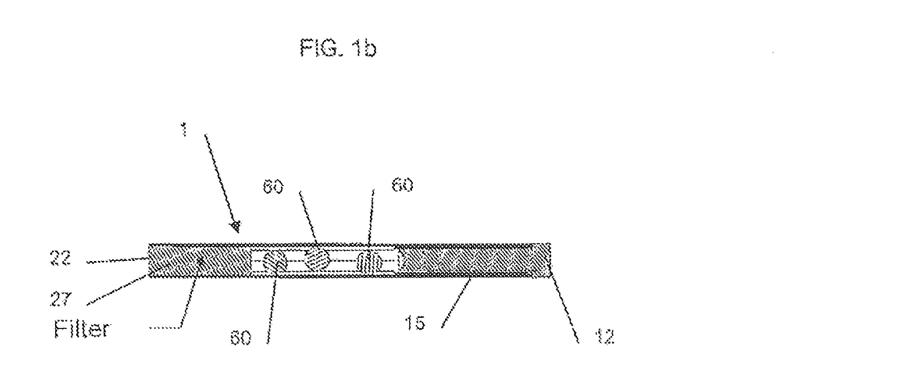
FIG. 1b is a view similar to that of FIG. 1a, but in the operative state of the inhalator.

The bodies (60) are movable together with said at least one substance from the first compartment (30) into the second compartment (40) to define an operative state of said inhalator (1) as shown in FIG. 1 b wherein the substances are contained in the second compartment (40) and wherein air entering through the air entry port (50) may take up, such as by evaporation, the at least one substance and be inhaled through said inhalation part (27).

In FIG. 1a and 1b is shown a pin (10) that the user uses to manually press the bodies (60) into the second compartment (40); the inhalator may be supplied to the user with the pin (10) already inserted partially into the first compartment (30) at the first open end (21).

As shown in FIGS. 1b and 3a-c the pin (10) has a head (12) and a plurality of longitudinally extending ribs (16); the ribs (16) preferably contact the inside surface (32) of the housing part defining the first compartment (30) with a slight frictional engagement. Between the ribs (16) are defined air flow channels (15) allowing air to flow in the first compartment (30) along the length of the pin (10) from the head (12) to the second compartment air entry port (50) after the bodies (60) have been pushed into the second compartment (40) by the pin. By the user varying the extent to which the pin is pushed forward towards the second compartment (40) the user may effectively control the amount of outside air mixed with the substances in the second compartment and inhaled through the mouth-piece, the pin acting as a valve.

Figure 3B:
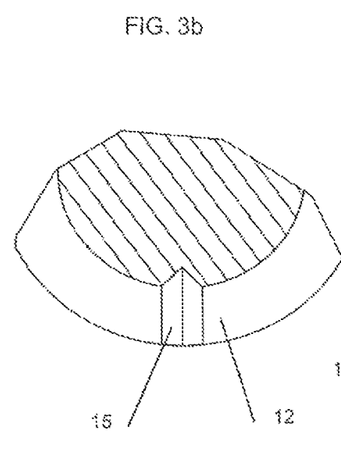
FIG. 3b is a cross-sectional view perpendicular to the longitudinal extension of the inhalator, showing a part of the pin at the head end thereof.
Figure 3C:
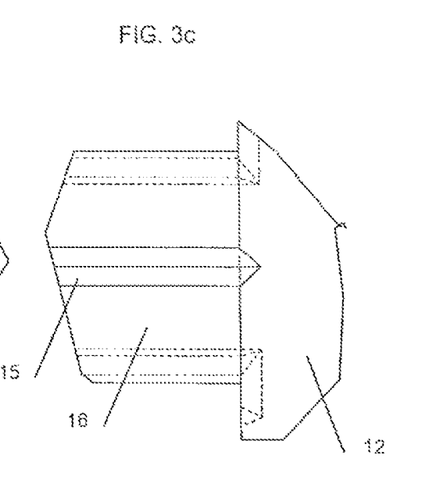
FIG. 3c is an enlarged longitudinal partial cross-section through the pin at the head end thereof.

The air flow channels (15) may constitute a V-shaped groove with varying/increasing width or depth to further adjustment of the air flow through the valve depending on the extent to which the pin is pushed forward towards the second compartment.

It is noted that the pin (10) preferably has a geometrical configuration (13) at the end opposite the head (12), corresponding in shape to that of the body (60) proximal to the pin (10) when arranged in the inoperative state, or the pin may have an concave end with a radius smaller than the body proximal to the pin to define a space between a sealing body and the end of the release device (10), to take up substances during activation.

The bodies (60) are preferably elastic and arranged such that a multiple number of chambers (62) will be created between the bodies. The bodies will due to their elasticity be restrained inside the first compartment (30). When in the operative state the bodies (60) would then expand towards slightly. The first compartment (30) may in principle have any geometrical shape as long as bodies complementary therewith may define sealed chambers (62); in the present embodiment, cylindrical compartments (30, 40) and spherical bodies (60) are envisaged although cylindrical bodies may also be used.

Figure 2B:
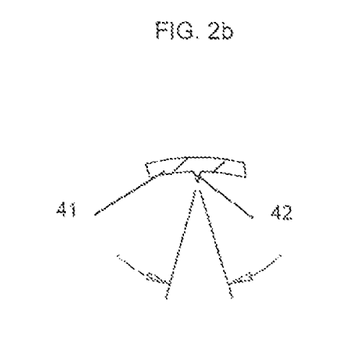
FIG. 2b is a cross-sectional view perpendicular to the longitudinal extension of the inhalator, showing a part of the side wall of the inhalator in the second compartment area, with a projecting pointed rib.

FIGS. 1a and 2a and 2b show how the cylindrical inside wall of the inhalator housing is preferably provided with a series of elongated pointed ribs (42) extending along the length of the second compartment (40); the second compartment (40) may have a larger cross section than the bodies (60) to optimize air flow around the bodies and, hence, mixing of air with the substances contained in the inhalator. To increase the exposed surface area of the bodies the spaced pointed ribs effectively provide surface(s) to which the bodies may adhere through the surface tension of any liquid substance contained in the inhalator and adhering to the surface of the bodies.

FIG. 2a shows that in the area of the air entry port (50) there may be provided an annular yielding constriction integrally molded with the inhalator wall (32).

The constriction may not only provide a slight resistance against the bodies (60) being moved into the second compartment (40) but also may provide a barrier against any liquids in the second compartment (40) tending to run back into the first compartment (30) in the operative state of the inhalator (1).

The inhalation part may include a barrier (27) preventing the elastic bodies from exiting said inhalator and having a central air passage with a configuration whereby air may pass into the passage even when one of the bodies (60) rests against said barrier; the central passage may have, seen in a cross sectional view through said barrier, a star-shaped configuration.

The first end (21) of the inhalator may be dimensioned and proportioned to be engageable with conventional nicotine-holding containers, such as products known as Nicotinell.

Figure 4:
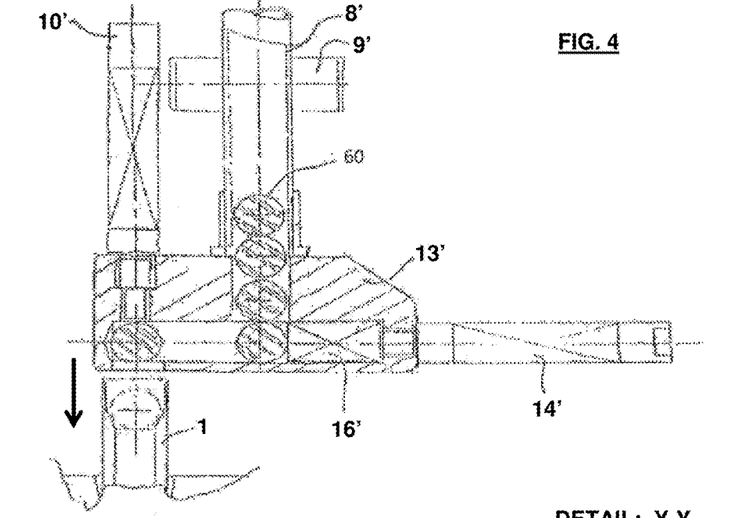
FIG. 4 shows schematically a device for filling the inhalator.

FIG. 4 illustrates a fixed frame (13') on which a number of air cylinders are mounted with a fixed ratio vertically, see (14') and (10').

From a filling tray the elastic bodies (60) are inserted through the tube (8') to avoid static electricity.

Use of photocell sensitivity control (9') secures complete filling of the tube.

The fixed inhalators (1) are placed in a device below (13') carried forward in a cycle. The row of elastic bodies is pushed forward by the air cylinders (14') and is delivered in the insertion position. Whenever the row of air cylinders (10') is activated, the ball unit is pressed downwards to its predetermined position inside the inhaler (1).

It should also be noted that upon activation of air cylinders (14') a sliding sleeve is dislocated (16') in order to prevent that any of the balls (60) are falling down prematurely.

The order shown is 100% automated and the ball units (60) are inserted section by section into 1 or more inhaler tubes carried forward.

To avoid confinement of air during insertion of the bodies, the fixed frame (13') may be further developed with a feeder sleeve compressing the ball (60) below the diameter required for the sealing process. Above sleeve is put into the inhaler tube before the balls are released and the sleeve is subsequently withdrawn as part of the filing process. This is not illustrated on FIG. 4.

The above description is also shown in detail: Y-Y.

The invention claimed is:

1. An inhalator comprising a housing with at least a first compartment and a second compartment, and including one or more substances, and a release device, said second compartment including at least one air entry port, said inhalator having a first proximal end of said first compartment and a second proximal end of said second compartment and a first distal end of the first compartment, a second distal end distal of the second compartment, the at least one entry port is at the second distal end, an inhalation part being at said second proximal end, said first compartment being for storing at least one substance and including in an inoperative state of said inhalator a plurality of sealing bodies arranged in a neighboring relationship, without the release device inserted into the housing, wherein being proximal is closest to a mouth of a user and being distal is furthest away from the mouth of said user;
  wherein at least one pair of neighboring sealing bodies defines at least in part a sealed chamber for containing a substance, said at least one pair of neighboring sealing bodies being movable together with said at least one substance from said first compartment into said second compartment to define an operative state of said inhalator;
  said operative state of the inhalator being a state;
    wherein said one or more substances are contained and are allowed to mix and blend in said second compartment;
    the release device is in the first compartment, and
    air entering through said at least one air entry port obtains at least a part of said at least one substance contained in said second compartment and is inhaled through said inhalation part while the release device is in the first compartment; and
  wherein said release device is for moving at least one of the sealing bodies from the first compartment to the second compartment when being inserted into the first compartment from the first distal end, and is configured to allow said air to flow to said at least one air entry port in the operative state, and the second compartment is located between the inhalation part and the first compartment.

2. The inhalator of claim 1, wherein said release device defines a valve allowing for a regulation of the flow of said air entering through said at least one air entry port.

3. The inhalator according to claim 2, wherein said release device allows for at least two values greater than zero of said flow of air entering through at least one of the at least one air entry port.

4. The inhalator according to claim 1, wherein said release device has a groove with a varying cross sectional area.

5. The inhalator according to claim 1, wherein said release device has a groove with an increasing cross sectional area.

6. The inhalator according to claim 1, wherein said release device is in frictional engagement with a surface of said first compartment.

7. The inhalator according to claim 1, wherein said release device defines an air flow conduit together with a surface of said first compartment.

8. The inhalator according to claim 1, wherein said release device includes an internal passage defining an air flow conduit for air flowing into said second compartment.

9. The inhalator according to claim 1, wherein said release device has a concave end opposite a head.

10. The inhalator according to claim 1, wherein said release device has a pin-like configuration.

11. The inhalator according to claim 1, wherein a cylindrical wall defines said second compartment including at least one air entry port.

12. The inhalator according to claim 1, wherein said second compartment has a larger inside cross-section than said bodies and has a surface configured to control a movement within said second compartment of said sealing bodies.

13. The inhalator according to claim 1, wherein said second compartment has a larger inside cross-section than said sealing bodies and has a surface including inwardly extending projections to control movement of said sealing bodies.

14. The inhalator according to claim 13, wherein said inwardly extending projections define pointed tips for facing said sealing bodies in said operative state.

15. The inhalator according to claim 1, wherein an inside transition to said second compartment includes an annular geometrical restriction for said sealing bodies.

16. The inhalator according to claim 1, wherein said inhalator includes at least two of said substances contained in a respective chamber.

17. The inhalator according to claim 1, wherein said second compartment is adapted to allow for said substances to be mixed when contained in said second compartment.

18. The inhalator according to claim 1, wherein said sealing bodies are elastic.

19. The inhalator according to claim 1, wherein said sealing bodies are formed as spheres.

20. The inhalator according to claim 1, wherein said inhalation part includes a barrier preventing said sealing bodies from exiting said inhalator and having a central air passage.

21. The inhalator according to claim 20, wherein said central air passage has a configuration allowing air to pass through said central air passage from said second compartment even when one of said sealing bodies rests against said barrier.

22. The inhalator according to claim 21, wherein said central air passage has, when seen in a cross sectional view through said barrier, a star-shaped configuration.

23. The inhalator according to claim 1, wherein one of said substances is tobacco, said tobacco being contained in said second compartment and/or in one of said chambers in said inoperative state.

24. The inhalator according to claim 23, wherein said tobacco is in a form of at least one tobacco leaf.

25. The inhalator according to claim 23, wherein one of said chambers or said second compartment includes said at least one tobacco leaf and another chamber including nicotine.

26. The inhalator according to claim 1, wherein said inhalation part is integral with said second compartment.

27. The inhalator according to claim 1, further comprising a wrapping extending at least partially around one or more of said inhalator part, said first compartment and/or said second compartment.

28. The inhalator according to claim 27, wherein said wrapping maintains said inhalator part, said first compartment and said second compartment in a contiguous relationship in extension of each other.

29. A method for manufacturing an inhalator according to claim 1, comprising steps of:
  providing the plurality of said sealing bodies, said plurality of sealing bodies being elastic;
  providing a framework having a fixture for the inhalator housing
  fixing said inhalator housing in said fixture;
  positioning a first of said plurality of sealing bodies in said first compartment by pushing said plurality of sealing bodies into said first compartment;
  dosing a first substance into said first compartment next to said first of said plurality of sealing bodies;
  positioning a second of said plurality of sealing bodies in said first compartment next to said first substance while compressing said second elastic body such that said first substance is enclosed in said first compartment formed by said first and second of said plurality of sealing bodies.

30. The inhalalor of claim 1, wherein said release device comprises a plurality of longitudinally extending ribs and air flow channels between the ribs.

31. The inhalalor of claim 1, wherein said inhalator is adapted to receive said release device at said first end being opposite said inhalation part being at said second end.

\* \* \* \* \*